United States Patent [19]
Elias

[11] Patent Number: 5,202,498
[45] Date of Patent: Apr. 13, 1993

[54] INHIBITING COLOR CHANGE IN CUMENE HYDROPEROXIDE

[75] Inventor: Carole L. Elias, Allegheny County, Pa.

[73] Assignee: Aristech Chemical Corporation, Pittsburgh, Pa.

[21] Appl. No.: 874,957

[22] Filed: Apr. 20, 1992

[51] Int. Cl.$^5$ .............................. C07C 409/10
[52] U.S. Cl. ........................ 568/559; 568/576
[58] Field of Search ............. 56/559; 568/576, 559, 568/562, 576

[56] References Cited

U.S. PATENT DOCUMENTS 2,527,640  10/1950  Lorand et al. .................. 568/559

FOREIGN PATENT DOCUMENTS 0029760  2/1983  Japan .................. 568/576
1366744  9/1974  United Kingdom .......... 568/559

*Primary Examiner*—Werren B. Lone
*Attorney, Agent, or Firm*—William L. Krayer

[57] ABSTRACT

Undesirable color change in freshly manufactured cumene hydroperoxide is inhibited by treatment comprising adding sodium hydroxide in an effective amount up to about 120 ppm and holding the treated cumene hydroperoxide at a temperature of about 50° C. to about 70° C. for 0.5 to two hours; optionally the cumene hydroperoxide so treated in the higher end of this caustic range is further treated with a wiped-film evaporator.

4 Claims, No Drawings

INHIBITING COLOR CHANGE IN CUMENE HYDROPEROXIDE

TECHNICAL FIELD

This invention relates to the preparation of cumene hydroperoxide for commercial sale and use, and particularly to the inhibiting or prevention of the onset of undesirable color change which otherwise may take place with time.

BACKGROUND OF THE INVENTION

Persons skilled in the art of manufacturing cumene hydroperoxide will recognize undesirable color of the product as a significant problem. The chemical mechanism by which undesirable color forms in the product is not well understood; the color bodies which cause the undesirable color are not readily identified and the factors which cause their formation have not been clearly recognized. It has been difficult to attack the problem without a clear understanding of its nature.

Moreover, the partial successes achieved empirically for color removal, after it has formed, seem to have no application to the prevention of color formation. Color formation can be accelerated by exposure to light and by heat; however, in industrial situations exposure to heat is the main cause of color formation, as light exposure is precluded by normal storage and handling procedures. Heat exposure is relatively commonplace; the ideal solution to the problem therefore is to provide a built-in mechanism to prevent or at least inhibit the formation of color under normal conditions of shipment and storage. The vagaries of the marketplace require protection over a wide range of conditions.

SUMMARY OF THE INVENTION

I have found that newly manufactured cumene hydroperoxide may be stabilized against color degradation for periods up to four weeks at temperatures of 85-90° F. by the addition of an effective amount, preferably about 15 to about 120 parts per million, of sodium hydroxide and holding the thus treated cumene hydroperoxide at a temperature of from about 50° to about 70° C. for a period of from about 0.5 to about two hours. Higher concentrations in this range, specifically about 80 to about 120 parts per million, enable the preparation of a color-stable product from which the caustic can be removed by means of a wiped-film evaporator, thus achieving a product that is color stable for up to two weeks at 85-90° F. without any increase in sodium content.

The test temperature range of 85-90° F. was chosen as a typical maximum temperature encountered in storage during the summer months. Although a minimum test time of two weeks was chosen, it is unlikely that cumene hydroperoxide ("CHP") would be exposed to such a high temperature for that long. Thus, the test is considered conservative.

While the present invention is applicable to any freshly made low-color CHP, it will be discussed primarily with respect to product made and purified according to the descriptions in U.S. Pat. No. 4,654,124, which is incorporated herein by reference.

DETAILED DESCRIPTION OF THE INVENTION

To determine if laboratory-derived CHP would be more color-stable than commercial CHP, cumene was oxidized in the laboratory and then concentrated using a laboratory wiped-film evaporator. The CHP thus made had an initial color of 8 APHA. However, the laboratory-derived CHP still exhibited color instability, increasing to 40 APHA after two weeks at 85-90° F., as shown in Table 1. Thus, the test did not indicate anything in particular with the oxidation which could account for the color instability of commercial CHP.

TABLE 1

COLOR TEST OF LABORATORY-MADE CHP

| | |
|---|---|
| MATERIAL: | CHP made by lab oxidation of cumene, followed by standard 2-pass wiped-film evaporator ("WFE") in laboratory. |
| CONDITIONS: | 85-90° F. |
| START COLOR: | 8 APHA |
| Day 1: | 11 APHA |
| Day 4: | 20 APHA |
| Day 5: | 42 APHA |
| Day 6: | 44 APHA |
| Day 7: | 39 APHA |
| Day 14: | 40 APHA |

Accordingly, emphasis shifted to trying to discover a treatment process which would stabilize the CHP color. The next set of tests is shown in Table 2. In these tests, several treatments were studied.

1. Two levels of caustic treatment were studied: 116 ppm NaOH and 77 ppm NaOH. The caustic treatment comprises heating the CHP product to 60° C., adding NaOH, and holding the CHP at 60° C. until the purple/pink color disappears. The purple/pink color is observed when the NaOH is first added to the CHP. The color gradually fades, with lighter initial colors fading to low APHA-scale colors faster than darker initial colors. Also, the lighter initial colors will show a pink color when the caustic is added, while dark yellow CHP will turn purple when caustic is added. Darker initial colors also require more caustic to achieve a stable low APHA color than does a lighter initial color. The 116 ppm NaOH level was arrived at by adding aqueous NaOH dropwise until further addition ceased to darken the purple shade. As the table indicates, the higher level of caustic resulted in a lower color at first, namely, 20 APHA. The lower level of caustic reduced the CHP color to 30 APHA at first, but the color was seen to decrease to 20 APHA after seven days at 85-90° F. In both cases, the CHP was at 20 APHA at the end of the two-week test at 85-90° F.

2. Another approach was to caustic treat the CHP product with 116 ppm NaOH, then a wiped-film evaporator was used to treat the CHP to remove the caustic. This process was considered in case the added sodium was perceived as objectionable. As Table 2 shows, the treated plus wiped film evaporated CHP was equally as stable as the CHP which was treated without removing the sodium afterwards. In this case, the color remained at 20 APHA for the entire two weeks at 85-90° F. Thus, the caustic appeared to destroy or remove the color precursors.

Wiped-film evaporators are known in the art and are described in the above-referenced U.S. Pat. No. 4,654,124.

3. A different approach was to caustic treat the crude CHP (the feed to the CHP refining or purification section) followed by purification using the standard 2-pass wiped-film evaporator. Commercially, this step would be done prior to the CHP refining system. An advantage to this method was that the sodium thus added would be removed in the existing wiped-film evaporators, resulting in a CHP product with a sodium level similar to that without the caustic treatment. The level of caustic, 371 ppm NaOH, was determined by adding NaOH until the purple color ceased to increase with additional caustic. The CHP product thus made was of good color—20 APHA, the same good color as was achieved by purification by the standard 2-stage wiped-film evaporator process. The color, however, was not stable at 85-90° F., increasing to 40 APHA after two weeks. It is not known why treating the wiped-film evaporator product with NaOH and then removing the caustic (method 2) is effective while treating the crude CHP prior to purification by the wiped-film evaporator and then removing the caustic is ineffective.

4. Another method tried was to caustic wash the crude CHP, followed by a decant and the standard 2-pass wiped-film evaporator. In the caustic wash, a separate water phase containing caustic was contacted with the CHP organic phase. This process could potentially treat the color-formers without adding more sodium to the crude CHP, since the sodium would remain in the water phase. In trying this method, causting-containing water was added to the crude CHP at 60° C. A pink color was observed in the water. Caustic was added until the organic phase turned milky white. The mixture was cooled and as much water as possible was decanted off. There was a large amount of water left in the organic phase. The water was easily removed in the laboratory wiped-film evaporator. In any case, this method resulted in less of a color improvement than with either caustic treating or 2-stage wiped-film evaporator treatment, and the color increased during storage at 85-90° F.

5. Thinking that perhaps the "lights" or the "heavies" in the crude CHP might contain the color-precursor(s), a 2-pass wiped-film evaporator pass was conducted in which larger than normal cuts were made to remove a higher amount of lights and heavies. The crude CHP was apparently unstable, as the product was initially low color but as the run progressed, darker material came overhead in the wiped-film evaporator. The color of this product was 90 APHA. It was decided not to test this product since it was already too dark.

6. Aged CHP product was subjected to an additional wiped-film evaporator step in an attempt to remove the color-bodies which formed over time in the untreated product. The product's initial color was 70 APHA and no improvement occurred in the wiped-film evaporator. This has been observed in the past, indicating that the non-volatile color-bodies in the crude CHP are different than the volatile color-bodies formed in storage. This CHP was not further tested.

7. A standard 2-pass wiped-film evaporation of the crude CHP was conducted as a control. This treatment actually was done prior to the "large cuts" (method 5) wiped-film evaporator. The 2-pass wiped-film evaporator resulted in a CHP product with a good initial color of 20 APHA. It is puzzling that the same feed would give a 20 color on one day and then a 90 color the next, but that is the nature of the CHP. This also argues against refrigeration as the sole means of stabilizing the CHP color, since this cannot help with these occasional spurts of particularly high-colored CHP product. The CHP thus made was stored at 85-90° F. for two weeks and exhibited the usual color instability, with a final color of 40 APHA.

TABLE 2

SCREENING OF POTENTIAL TREATMENTS

| START COLOR: | CHP Product | 70 APHA |
| | Crude CHP | 300 APHA |

VARIOUS TREATMENTS STUDIED:
1. Caustic Treat CHP product with 116 ppm NaOH
2. Caustic Treat CHP Product with 77 ppm NaOH
3. Caustic Treat CHP Product with 116 ppm NaOH, then WFE
4. Caustic Treat Crude CHP with 371 ppm NaOH, then WFE
5. Caustic Wash Crude CHP, decant water, then WFE
6. Large Cuts of Crude CHP
7. WFE of CHP Product
8. Standard Lab WFE of Crude CHP

TEST TEMPERATURE: 85° F.

| TREATMENT | 0 | 1 | 3 | 6 | 7 | 8 | 9 | 10 | 13 | 14 |
|---|---|---|---|---|---|---|---|---|---|---|
| 1. CT CHP Product (116 ppm NaOH) | 20 | 20 | 20 | 20 | 20 | 20 | 20 | 20 | 20 | 20 |
| 2. CT CHP Product (77 ppm NaOH) | 30 | 30 | 30 | 30— | 20 | 20 | 20 | 20 | 20 | 20 |
| 3. CT CHP Product (116 ppm) + WFE | 20 | 20 | 20 | 20 | 20 | 20 | 20 | 20 | 20 | 20 |
| 4. CT + WFE Crude CHP (371 ppm) | 20 | 20 | 20 | 30 | 30 | 40 | 40 | 40 | 40 | 40 |
| 5. CW + WFE Crude CHP | 30 | 30 | 30 | 40 | 40 | 40 | 40 | 40 | 50 | 50 |
| 6. Large Cuts of Crude CHP | 90 | NOT TESTED (TOO DARK) | | | | | | | | |
| 7. WFE of Dark CHP Product | 90 | NOT TESTED (TOO DARK) | | | | | | | | |
| 8. Std WFE Crude CHP | 20 | 20 | 30 | 40 | 40 | 40 | 40 | 40 | 40 | 40 |

CT = Caustic Treat
CW = Caustic Wash
WFE = wiped-film evaporator

Since the CHP used in the previous tests showed signs of being particularly bad with respect to color instability, a second set of tests was performed using a more normal commercial CHP. This material exhibited no unusual changes in color during processing, as did the previous material. The treatments, the results of which are shown in Table 3, are as follows:

A. Since in the last set of treatments 75 ppm NaOH performed as well as 116 ppm NaOH, and with more unstable CHP, the caustic treatment tests were repeated using 75 ppm NaOH as the high level for comparison. The low level was 14 ppm NaOH. The untreated CHP had a color of 30 APHA. After treatment with either level of caustic, the color was reduced to 10 APHA. The samples were then held at 85-90° F. for two weeks. The 75 ppm material remained at 10 APHA the entire time, while the 14 ppm material increased slightly to 20 APHA. This indicated that perhaps a slightly higher level of caustic than the 14 ppm would be required, particularly with higher color feeds.

B. The caustic treatment of CHP product followed by a wiped-film evaporator step to remove the caustic was repeated at the 75 ppm and 14 ppm NaOH levels. These steps also resulted in an initial color of 10 APHA for both levels of caustic. The CHP thus treated with the lower levels of caustic than the previous tests were not color stable. The 75 ppm material increased to 30 APHA after two weeks at 85-90° F., and the 14 ppm material increased to 30+ APHA. Thus, it would appear that a higher level of caustic is required for color stability when treating CHP product if it is necessary to then remove the caustic in the wiped-film evaporator.

C. The caustic treatment of the crude CHP prior to the 2-pass wiped-film evaporator was repeated, using the more stable crude CHP. This was to ensure that the failure of the color stability test was not due to the unusually bad starting material. In this treatment the crude CHP was treated with 78 ppm NaOH, followed by a 2-pass wiped-film evaporator. The resulting product had a color of 20 APHA, as opposed to 10 APHA obtained by treating the wiped-film evaporator product with the same amount of caustic. Again, the CHP thus treated was unstable, with the color increasing to 40+ APHA after two weeks at 85-90° F.

D. The "large cuts" wiped-film evaporator was repeated using the good CHP. This treatment yielded a color of 10 APHA initially. The color increased to 50 APHA after the two-week test.

E. An alternate method was tried whereby the caustic treatment of the CHP was performed after the crude CHP was run through the first pass wiped-film evaporator and before the second pass wiped-film evaporator. Since treating the feed to the first pass did not work, but treating the product did, there was a chance that treating the intermediate product might be effective. About 96 ppm NaOH was required to treat the intermediate CHP. The CHP made by this method had a color of 10+ APHA. The color increased to 50 APHA during the two-week test at 85-90° F.

F. As a control, the crude CHP was run through the laboratory wiped-film evaporator in two passes to generate a fresh CHP product for testing. This CHP had an initial color of 10 APHA, but the color increased to 50 APHA during the test.

G. Two other controls were tested since the samples obtained from the plant of fresh CHP and CHP product were low in color (after shipment). These samples were tested to determine if they exhibited any color stability at warm storage temperatures. However, the fresh CHP increased from 20+ APHA to 40 APHA during the test and the CHP product increased from 30 APHA to 40+ APHA.

TABLE 3

FURTHER SCREENING TESTS OF POTENTIAL CHP TREATMENTS

| START COLOR: | CHP Product | 30 APHA |
| | Fresh CHP* | 20 APHA |
| | Crude CHP | 200 APHA |

VARIOUS TREATMENTS STUDIED:
1. CT CHP Product with 75 ppm NaOH
2. CT CHP Product with 14 ppm NaOH
3. CT CHP Product with 75 ppm NaOH, then WFE
4. CT CHP Product with 14 ppm NaOH, then WFE
5. CT Crude CHP with 78 ppm NaOH, then WFE
6. Large Cuts of Crude CHP
7. First-Pass WFE of Crude CHP, Caustic Treat the residue with 96 ppm NaOH, then second-pass WFE
8. Standard Lab WFE of Crude CHP

| TREAT-MENT | TEST TEMPERATURE: 85-90° F. DAYS | | | | | | | |
| --- | --- | --- | --- | --- | --- | --- | --- | --- |
| | 0 | 3 | 5 | 7 | 10 | 12 | 13 | 14 |
| Fresh CHP | 20+ | 20+ | 20+ | 40 | 40 | 40 | 40 | 40 |
| CHP Product | 30 | 30+ | 30+ | 30+ | 40 | 40 | 40+ | 40+ |
| 1. CHP Product (75 ppm NaOH) | 10 | 10 | 10 | 10 | 10 | 10 | 10 | 10 |
| 2. CHP Product (14 ppm NaOH) | 10 | 10 | 10 | 20 | 20 | 20 | 30 | 20 |
| 3. CHP Product + WFE (75 ppm) | 10 | 10 | 10 | 20 | 20 | 30 | 30 | 30 |
| 4. CHP Product + WFE (14 ppm) | 10 | 20 | 20 | 20 | 30 | 30+ | 30+ | 30+ |
| 5. CT + WFE Crude CHP (78 ppm) | 20 | 30 | 40 | 40 | 30+ | 40 | 40+ | 40+ |
| 6. WFE Crude CHP, Large Cuts | 10 | 30+ | 40 | 40 | 40 | 40+ | 50 | 50 |
| 7. WFE Crude CHP + NaOH + WFE | 10+ | 20 | 30 | 40 | 40 | 50 | 50 | 50 |
| 8. Std WFE Crude CHP | 10 | 20+ | 30 | 40 | 40 | 40+ | 50 | 50 |

| EXTENDED TESTS: | 3 WEEKS | 4 WEEKS | 5 WEEKS |
| --- | --- | --- | --- |
| 1. CT CHP Product (75 ppm NaOH) | 10 | 20 | 30 |
| 2. CT CHP Product + WFE (75 ppm) | 30+ | 40 | |
| 3. CT CHP Product (14 ppm NaOH) | 30 | 40 | |

*Newly-refined CHP stored temporarily upstream of CHP Product
CT = Caustic Treat
WFE = wiped-film evaporator Since the laboratory results indicated that treating the CHP product with caustic was the most practical method for stabilizing the CHP color, the emphasis shifted to determining the process requirements for the treatment.

The first study looked at three variables: level of caustic (72 ppm versus 36 ppm), treatment time (thirty minutes versus one hour), and the effect of stirring during treatment. The results are shown in Table 4.

The study used a sample of CHP Product which had an initial color of 20 APHA. As before, the CHP would be heated to 60° C. prior to adding the aqueous NaOH. For the stirring case, the stirring of the CHP would be continued for the entire treatment time. For the other case, the CHP would be stirred for the first five minutes of treatment to ensure good dispersion of the caustic, while the remainder of the treatment would be conducted without stirring. This latter case was to simulate the effect of a static mixer followed by a baffled tank.

Two dependent variables were studied in these tests. One was the color stability of the treated CHP. The other was the initial color immediately following treatment. As previously mentioned, the CHP undergoes a color change during the caustic addition step. This pink color fades during the treatment. Until the pink color completely fades, however, the CHP color as determined either by APHA tubes or colorimeter may even exceed the initial color. Accordingly, the CHP treated for sixty minutes had a lower initial color than the CHP treated for only thirty minutes. Also, the CHP treated with 36 ppm NaOH had a higher initial color than the CHP treated with 72 ppm NaOH. The amount of stirring did not appear to have any noticeable effect on initial color.

The treated CHP was held at 85-90° F. for fifteen days. As Table 4 shows, there did not appear to be any significant difference in color according to the various treatments. Although the one sample showed a 10 APHA color versus the rest of the treated CHP's having a 20 APHA, these colors were read by color tube rather than colorimeter. As low colors are extremely difficult to read using the tubes, the difference reported may not be real. In any case, the untreated CHP increased in color from 20 to 50 APHA in the same time.

The test was continued for an additional week. This time the colors were read by colorimeter. No significant difference in color was detected among the treated samples, with the color remaining at about 15-20 APHA after three weeks at the warm temperature.

Thus, the study indicated several things. First, there was no effect seen between stirring the entire time versus stirring only for the first five minutes. Also, 36 ppm NaOH was as effective as 72 ppm. Since, an earlier study had shown that an even lower level of 14 ppm was effective, but marginal at extended test times, 30 ppm NaOH was selected as the design level of caustic for the caustic treatment process. The study also showed that a one-hour treatment time was not sufficient for the pink color to fade at the 36 ppm caustic level. Thus, a longer treatment time was indicated.

TABLE 4

CAUSTIC TREATMENT DESIGN VARIABLES STUDY

1. CHP Product + 72 ppm NaOH + 30 min. stirring
2. CHP Product + 72 ppm NaOH + 5 min. stirring + 25 min. not stirring
3. CHP Product + 72 ppm NaOH + 60 min. stirring
4. CHP Product + 72 ppm NaOH + 5 min. stirring + 55 min. not stirring
5. CHP Product + 36 ppm NaOH + 5 min. stirring + 25 min. not stirring
6. CHP Product + 36 ppm NaOH + 5 min. stirring + 55 min. not stirring

| | INITIAL* | DAYS | | | | | | | |
|---|---|---|---|---|---|---|---|---|---|
| | | 0 | 1 | 2 | 7 | 8 | 12 | 15 | 22 |
| CHP Product | 20 | 20 | 20 | 21 | 35 | 32 | 40 | 50 | 42 |
| 1. 72 ppm/30 + 0 | 26 | 22 | 15 | 15 | 18 | 10 | 10 | 10 | 16 |
| 2. 72 ppm/5 + 25 | 28 | 16 | 18 | 17 | 11 | 13 | 20 | 20 | 23 |
| 3. 72 ppm/60 + 0 | 20 | 12 | 9 | 11 | 9 | 9 | 20 | 20 | 18 |
| 4. 72 ppm/5 + 55 | 23 | 20 | 14 | 15 | 17 | 12 | 20 | 20 | 13 |
| 5. 36 ppm/5 + 25 | 52 | 21 | 11 | 2 | 10 | 10 | 20 | 20 | 17 |
| 6. 36 ppm/5 + 55 | 41 | 12 | 11 | 13 | 9 | 11 | 20 | 20 | 13 |

*Initial color refers to color immediately after treatment. Actual color may continue to decrease after treatment, depending on length of heating time.

Since the last study showed that 30 ppm NaOH was a good level to use, the only remaining variable was treatment time. Three treatment times were tested: one hour, 90 minutes, and two hours. As before, the treatment times consisting of five minutes of stirring, with the remainder of the time using no stirring.

The initial color was read immediately after each treatment. The results are shown in Table 5. The CHP treated for only one hour had a slightly darker initial color due to insufficient time for the pink color to fade than the untreated CHP. The CHP treated for longer than one hour was lighter than the untreated CHP. The CHP was tested at 85-90° F. for a period of two weeks. The untreated CHP increased in color to 60 APHA.

The treated CHP remained at 30 APHA, except for the one-hour case which showed a 40 APHA. This difference is within the limits of accuracy of the color reading method, however.

The tests indicated that probably the 90-minute treatment time would be sufficient. However, since darker CHP requires longer treatment times, the two-hour treatment time was selected for the design.

TABLE 5

CAUSTIC TREATMENT DESIGN VARIABLE STUDY USING CHP

1. CHP Product + 30 ppm NaOH + 5 min. stirring + 55 min. not stirring
2. CHP Product + 30 ppm NaOH + 5 min. stirring + 85 min. not stirring
3. CHP Product + 30 ppm NaOH + 5 min. stirring + 115 min. not stirring

| | INITIAL* | DAYS | | | |
|---|---|---|---|---|---|
| | | 0 | 1 | 8 | 14 |
| Untreated CHP Product | 42 | 53 | 47 | 50 | 60 |
| 1. 30 ppm/5 + 55 | 49 | 51 | 31 | 30 | 40 |
| 2. 30 ppm/5 + 85 | 30 | 29 | 30 | 30 | 30 |
| 3. 30 ppm/5 + 115 | 36 | 39 | 35 | 30 | 30 |

*Initial color refers to color immediately after treatment. Actual color may continue to decrease after treatment, depending on length of heating time.

As a final test, freshly refined CHP product was treated on-site at a commercial plant. The test used the tentative design conditions of 30 ppm NaOH and a treatment time of two hours at 60° C. CHP from an intermediate storage tank on a CHP refining skid was the material used for the treatment. This is the CHP product as made, fresh from the unit. The untreated CHP had a color of 24 APHA. The color of the CHP after treatment was 18 APHA. Both samples of CHP were then shipped to the laboratory for the storage test. As Table 6 shows, the untreated CHP increased to 46 APHA during shipment, while the treated CHP arrived with a color of 20 APHA.

The two samples of CHP were stored at 85-90° F. for a period of two weeks. At the end of the test period, the untreated CHP had increased in color to 83 APHA, while the treated CHP was only slightly increased to 27 APHA.

TABLE 6

CAUSTIC TREATMENT ON-SITE AT PLANT

1. Untreated Fresh CHP: initial color 24 APHA
2. Fresh CHP + 30 ppm NaOH at 140° F. for two hours: color after treatment 18 APHA

| | | APHA COLOR DAYS | | | | |
|---|---|---|---|---|---|---|
| SAMPLE | PLANT | 0 | 4 | 8 | 11 | 14 |
| 1. Fresh CHP | 24 | 46 | 66 | 73 | 72 | 83 |
| 2. Fresh CHP + 30 ppm NaOH | 18 | 20 | 16 | 24 | 26 | 27 |

As a check that the treatment does not degrade the CHP chemically, a GC analysis was obtained for both the treated and untreated CHP. these analyses are shown in Table 7. The analyses show no real change between samples, with both CHP's being about 94% CHP.

TABLE 7
COMPARISON OF GC ANALYSES OF TREATED VS UNTREATED CHP

|  | Untreated Fresh CHP | Treated Fresh CHP |
|---|---|---|
| Cumene | 0% | 0% |
| Acetophenone | .74% | .90% |
| DMBA | 5.07% | 5.18% |
| CHP | 94.18% | 93.92% |

An additional test was performed to see if any detectable substances were formed during the treatment of CHP due to the addition of NaOH. A sample of CHP product was handled in two different ways: (1) heat the CHP to 60° C. and hold at this temperature for two hours, with no addition of NaOH, and (2) the "standard" caustic treatment whereby 30 ppm of NaOH is added to the CHP, which is then held at 60° C. for two hours. The control sample was heated in case the thermal treatment caused any noticeable decomposition, although this was considered unlikely. As Table 8 shows, the LC analysis did not detect any differences in composition between the two samples. This does not mean that no substances were formed, just that none were detectable with the current analytical capabilities.

TABLE 8
COMPARISON OF LC ANALYSES OF TREATED VS UNTREATED CHP

| 1. | CHP Product with no caustic, held at 60° C. for 2 hours | |
|---|---|---|
| 2. | CHP Product + 30 ppm NaOH, held at 60° C. for 2 hours | |

|  | 1. Untreated CHP Product | 2. Treated CHP Product |
|---|---|---|
| Cumene | 0.1% | 0.1% |
| Acetophenone | .9% | .9% |
| DMBA | 6.6% | 6.6% |

An additional test was done to determine the time limits for storage stability of the caustic-treated CHP. The results are shown in Table 9. The CHP used for the test had an initial color of 15 APHA. After caustic treatment, the CHP was slightly reduced in color to 10 APHA. The treated CHP remained at 10 APHA after three weeks at 90° F., with a negligible increase in color to 15 APHA after four weeks. The untreated CHP increased to 40 APHA over the same time period. Thus the caustic treatment results in a superior color-stable product.

My most preferred process comprises heating the CHP to about 60° C. (50-70°), adding 30 ppm of NaOH with mixing, and holding the CHP at 60° C. in a baffled tank for a period of about two hours (at least about 0.5 hours). Laboratory tests have shown that such a process will result in a color-stable CHP at temperatures up to 90° F. for a period of four weeks.

TABLE 9
EXTENDED STORAGE TEST FOR CAUSTIC-TREATED CHP

1. CHP + 30 ppm NaOH, held at 60° C. for 2 hours
2. Untreated CHP

|  | APHA COLOR | | | |
|---|---|---|---|---|
|  | START | 2 WKS @ 90° F. | 3 WKS @ 90° F. | 4 WKS @ 90° F. |
| 1. CHP + 30 ppm NaOH | 10 | 10 | 10 | 15 |
| 2. Untreated CHP | 15 | 20 | 30 | 40 |

I claim:

1. Method of treating freshly manufactured cumene hydroperoxide to inhibit color formation comprising adding thereto about 15 ppm to about 120 ppm of sodium hydroxide and maintaining the cumene hydroperoxide so treated at a temperature of from about 50° C. to about 70° C. for a period of about 0.5 to about two hours.

2. Method of claim 1 wherein the amount of sodium hydroxide added is about 80 ppm to about 120 ppm.

3. Method of claim 1 following by passing the product so treated through a wiped-film evaporator to remove the sodium hydroxide.

4. Method of inhibiting undesired color formation in newly manufactured cumene hydroperoxide comprising heating said cumene hydroperoxide to about 50° C. to about 70° C., adding about 30 ppm NaOH thereto, and holding the cumene hydroperoxide at about 60° C. for at least about 1.5 hours.

* * * * *

UNITED STATES PATENT AND TRADEMARK OFFICE
CERTIFICATE OF CORRECTION

PATENT NO. : 5,202,498
DATED : April 13, 1993
INVENTOR(S) : Carole L. Elias

It is certified that error appears in the above-identified patent and that said Letters Patent is hereby corrected as shown below:

Column 10, line 36, claim 3, change "following" to -- followed --.

Signed and Sealed this

Fourth Day of January, 1994

Attest:

BRUCE LEHMAN

*Attesting Officer*  *Commissioner of Patents and Trademarks*